(12) United States Patent
Wang et al.

(10) Patent No.: US 9,675,542 B2
(45) Date of Patent: Jun. 13, 2017

(54) ORAL CARE COMPOSITIONS

(75) Inventors: Wei Wang, Plainsboro, NJ (US); Harsh M. Trivedi, Hillsborough, NJ (US); Mahmoud Hassan, Somerset, NJ (US)

(73) Assignee: Colgate-Palmolive Company, New York, NY (US)

( * ) Notice: Subject to any disclaimer, the term of this patent is extended or adjusted under 35 U.S.C. 154(b) by 349 days.

(21) Appl. No.: 14/114,855

(22) PCT Filed: May 14, 2012

(86) PCT No.: PCT/US2012/037687
§ 371 (c)(1),
(2), (4) Date: Oct. 30, 2013

(87) PCT Pub. No.: WO2012/158580
PCT Pub. Date: Nov. 22, 2012

(65) Prior Publication Data
US 2014/0065080 A1    Mar. 6, 2014

Related U.S. Application Data

(60) Provisional application No. 61/486,356, filed on May 16, 2011, provisional application No. 61/486,349, filed on May 16, 2011, provisional application No. 61/486,352, filed on May 16, 2011, provisional application No. 61/486,354, filed on May 16, 2011, provisional application No. 61/486,371, filed on May 16, 2011, provisional application No. 61/486,359, filed on May 16, 2011, provisional application No. 61/486,366, filed on May 16, 2011.

(51) Int. Cl.
| A61K 8/97 | (2017.01) |
| A61Q 11/00 | (2006.01) |
| A61K 8/34 | (2006.01) |

(52) U.S. Cl.
CPC .............. *A61K 8/97* (2013.01); *A61K 8/345* (2013.01); *A61Q 11/00* (2013.01)

(58) Field of Classification Search
USPC .................................................. 424/401, 732
See application file for complete search history.

(56) References Cited

U.S. PATENT DOCUMENTS

| 4,894,220 | A | 1/1990 | Nabi et al. |
| 5,980,869 | A | 11/1999 | Sanker et al. |
| 6,117,417 | A * | 9/2000 | Wicks et al. ................ 424/54 |
| 6,855,346 | B2 | 2/2005 | Wu |
| 6,949,264 | B1 | 9/2005 | McGrew et al. |
| 2003/0147969 | A1 | 8/2003 | Wu |
| 2003/0170322 | A1 | 9/2003 | Kayane et al. |
| 2004/0126441 | A1 | 7/2004 | Pushpangadan et al. |
| 2004/0180077 | A1 | 9/2004 | Riker et al. |
| 2004/0247532 | A1 | 12/2004 | Pinol et al. |
| 2004/0253192 | A1 | 12/2004 | Maxwell et al. |
| 2005/0226822 | A1 | 10/2005 | Garbers et al. |
| 2005/0233004 | A1 | 10/2005 | Shin et al. |
| 2006/0062859 | A1 | 3/2006 | Blum et al. |
| 2006/0134235 | A1 * | 6/2006 | Takagaki et al. ............ 424/732 |
| 2006/0177384 | A1 | 8/2006 | Brown |
| 2007/0003502 | A1 | 1/2007 | Tanabe et al. |
| 2007/0190090 | A1 | 8/2007 | Brown |
| 2007/0297993 | A1 | 12/2007 | Kindel et al. |
| 2009/0092688 | A1 | 4/2009 | Williams et al. |
| 2009/0220625 | A1 | 9/2009 | Herrmann et al. |
| 2010/0022471 | A1 | 1/2010 | Hanifl et al. |
| 2010/0028318 | A1 | 2/2010 | Saito et al. |
| 2010/0055138 | A1 * | 3/2010 | Margulies et al. ........... 424/401 |
| 2010/0068166 | A1 | 3/2010 | Fowler |
| 2010/0098791 | A1 | 4/2010 | Rodriguez-Vilaboa |
| 2010/0152118 | A1 | 6/2010 | Shailubhai |
| 2010/0278944 | A1 | 11/2010 | Scholey et al. |

FOREIGN PATENT DOCUMENTS

| CN | 101849979 | 10/2010 |
| CN | 101970008 | 2/2011 |
| EP | 1293131 | 3/2003 |
| EP | 1487406 | 10/2003 |
| EP | 1793799 | 6/2007 |
| EP | 2039356 | 3/2009 |
| EP | 2127646 | 12/2009 |
| EP | 1575670 | 9/2010 |
| GB | 1438205 A | 6/1976 |
| GB | 2317339 A | 3/1998 |
| JP | 2002-173425 | 6/2002 |
| JP | 2004-359595 | 12/2004 |
| JP | 2005-529125 A | 9/2005 |
| WO | WO 02/094297 | 11/2002 |
| WO | WO 03/030822 | 4/2003 |
| WO | WO 2006/128032 | 11/2006 |
| WO | WO 2007/092811 | 8/2007 |

(Continued)

OTHER PUBLICATIONS http://big5.china.com.cn/info/2011-02/21/content_21968923.htm, "Pomegranate", Feb. 21, 2011.
Buckley et al;., "Antagonist binding properties of five cloned muscarinic receptors expressed in CHO-K1 cells," Am. Society for Pharm. and Exper. Therapeutics, 35(4):469-476, Apr. 1989.
Certificate of Analysis, Ginger Powder Extract, Manufacture Date Mar. 18, 2010.
Certificate of Analysis, Grape Seed Extract, Manufactured May 10, 2010.
Certificate of Analysis, Grape Seed Powder Extract, Manufacture Date Mar. 9, 2010.
Certificate of Analysis, Panax Ginseng Powder Extract, Manufacture Date Apr. 27, 2010.
Certificate of Analysis, Prunella Powder Extract, Manufacture Date Apr. 21, 2010.
Dorje et al., "Antagonist binding profiles of five cloned human muscarinic receptor subtypes," Am. Society for Pharm. and Exper. Therapeutics, 256(2):727-733, Feb. 1991.

(Continued)

*Primary Examiner* — Walter Webb

(57) ABSTRACT

Described herein are oral compositions comprising an extract obtained from Arialaceae, Zingiberaceae, Lamiaceae, Fabaceae, Solanaceae, Punicaceae. Asteraceae or mixtures thereof; Their uses for alleviating dry mouth is also described.

3 Claims, No Drawings

(56) References Cited

FOREIGN PATENT DOCUMENTS

| WO | WO 2007/092823 | 8/2007 |
|---|---|---|
| WO | WO 2008/045579 | 4/2008 |
| WO | WO 2009/050479 | 4/2009 |
| WO | WO 2010/057034 | 5/2010 |
| WO | WO 2010/099062 | 9/2010 |
| WO | WO 2010/129307 | 11/2010 |
| WO | WO 2011/068811 A1 | 6/2011 |

OTHER PUBLICATIONS

Ghayur et al., "Cardiovascular effects of ginger aqueous extract and its phenolic constituents are mediated through multiple pathways," Vascul Pharmacol. Oct. 2005, 43(4):234-41.

Ghayur et al., "Ginger facilitates cholinergic activity possibly due to blockade of muscarinic autoreceptors in rat stomach fundus," Pak J Pharm Sci, Jul. 2007;20(3):231-5.

Ghayur et al., "Muscarinic, Ca(++) antagonist and specific butyrylcholinesterase inhibitory activity of dried ginger extract might explain its use in dementia," J Pharm Pharmacol. Oct. 2008;60(10):1375-83.

ISR & Written Opinion for PCT/US2012/037687 mailed on Nov. 19, 2012.

Mintel, "Energy and breath freshener," Database Accession No. 1209441, Nov. 2009.

Mintel, "Organic mouthwash spray," Database Accession No. 10107001, Apr. 2002.

Mintel, "Toothpaste," Database Accession No. 728223, Jun. 2007.

Park et al., "Effects of Korean red ginseng on dry mouth: a randomized, double-blind, placebo-controlled trial," Journal of Ginseng Research, 34(3):183-191, 2010.

Pertz et al., "Effects of ginger constituents on the gastrointestinal tract: role of cholinergic M3 and serotonergic 5-HT3 and 5-HT4 receptors," Planta Med. Jul. 2011;77(10):973-8.

Pitman, "Aloe vera gets thumbs up as natural oral care ingredient," Cosmeticsdesign.com, Jul. 28, 2009, retrieved from http://www.cosmeticsdesign.com/content/view/print/254804.

Proctor, "Muscarinic receptors and salivary secretion," J. Appl. Physiol., 100:1103-1104, 2006.

Tachikawa et al., "Effects of ginseng saponins on responses induced by various receptor stimuli," Eur J Pharmacol. Mar. 12, 1999; 369( 1 ):23-32.

Tobin et al., "Rapid agonist-mediated phosphorylation of m3-Muscarinic receptors revealed by immunoprecipitation," J. of Biological Chemistry, 268(13): 9817-9828, 1993.

Database GNPD [Online] Mintel; Mar. 2011, "Dry Mouth Anticavity Fluoride Rinse," XP002762321, Database accession No. 1517366.

Chamani, Goli et al., "Evaluation of Effects of *Zingiber officinale* on Salivation in Rats," Acta Medica Iranica, vol. 49, No. 6 (2011) pp. 336-340.

Database GNPD [Online] Mintel; Sep. 2010, "Moisturising Mouthwash," XP002762323, Database accession No. 1409229.

\* cited by examiner

ORAL CARE COMPOSITIONS

This application is a national stage entry under $5 U.S.C. §371 of International Patent Application No. PCT/US2012/037687, filed 14 May 2012, which claims priority to U.S. Provisional Patent Application Ser. No. 61/486,356, filed on 16 May 2011, U.S. Provisional Patent Application Ser. No. 61/486,349, filed on 16 May 2011, U.S. Provisional Patent Application Ser. No. 61/486,352, filed on 16 May 2011, U.S. Provisional Patent Application Ser. No. 61/486,354, filed on 16 May 2011, U.S. Provisional Patent Application Ser. No. 61/486,371, filed on 16 May 2011, U.S. Provisional Patent Application Ser. No. 61/486,359, filed on 16 May 2011 and U.S. Provisional Patent Application Ser. No. 64/486,366, filed on 16 May 2011, each of which is incorporated herein by reference.

BACKGROUND

Xerostomia refers to dry mouth caused by a lack of saliva and is often associated with some form of salivary gland dysfunction.

In the field of oral care, xerostomia is problematic as saliva provides a protective effect on the teeth and can dilute or wash away harmful bacteria and/or food particles from the oral cavity. Failure to protect the teeth or allowing an accumulation of harmful bacteria/food particles can lead to bad breath (halitosis) or more seriously, to infections of the mucosal or periodontal tissue of the oral cavity.

Although M3 receptor agonists are known, e.g. pilocarpine, their use is limited by potential interactions with concomitant medications and/or medical conditions. Therefore, a need still exists in the art for alternative agents and compositions for the treatment of xerostomia (dry mouth).

SUMMARY

In some embodiments the present invention provides an oral care composition for use in treating dry mouth, comprising: a dry mouth component comprising an oligosaccharide or a ginsenoside, and a polymer; and an orally acceptable carrier. In some embodiments, the dry mouth component comprises an extract of Arialaceae, Zingiberaceae, Lamiaceae, Fabaceae, Solanaceae, Punicaceae, Asteraceae or a combination of two or more thereof. In some embodiments, the compositions of the present invention increase salivation, alleviate dry mouth and the sensations of dry mouth, and/or maintain or improve oral hygiene. Some embodiments of the present invention provide a method for increasing salivation, alleviating dry mouth and the sensations of dry mouth, comprising administering to the oral cavity of a subject in need thereof an effective amount of an oral care composition as described herein.

The present invention provides a composition that includes an extract from Arialaceae, Zingiberaceae, Lamiaceae, Fabaceae, Solanaceae, Punicaceae, Asteraceae or mixtures thereof in an amount sufficient to promote the above goals and an oral carrier for the extract. A suitable amount of the Asteraceae extract is from 0.6 to 1.5 weight percent of the overall composition. A suitable amount of the Arialaceae, Lamiaceae, Fabaceae extract is from 0.15 to 0.75 weight percent of the overall composition. A suitable amount of the Solanaceae extract is from 0.025 to 0.075 weight percent of the overall composition. A suitable amount of the Punicaceae extract is from 0.075 to 0.75 weight percent of the overall composition. A suitable amount of the Zingiberaceae extract is from 0.001 to 0.025 weight percent of the overall composition. Preferably, the extract is present in an amount sufficient to provide the above benefits for a prolonged period, i.e., for one minute or more.

Regardless of the particular form of the compositions, the compositions include an extract of Arialaceae, Zingiberaceae, Lamiaceae, Fabaceae, Solanaceae, Punicaceae, Asteraceae or mixtures thereof, as the active component, and a carrier for the extract that is suitable for oral use. When taken or administered orally, the compositions promote increased salivation and improved oral hygiene, and/or a variety of desirable sensations. They may enhance and potentiate other flavorings used in commercial products.

One means of testing the effectiveness of a potential M3 muscarinic cholinergic receptor agonist is to utilize the calcium mobilization assay for determining agonist activity of the human M3 receptor with agonist activity being a means for determining the likelihood of saliva formation and thereby treating xerostomia.

As used herein, oral hygiene refers to acceptable or good health in terms of salivation, freshness of breath, dental condition, gum condition, condition of oral mucosa, condition of an oral bio-film, condition of oral bacteria or oral plaque, and/or the like, as well as other specific conditions described herein. Further, as used herein, promoting refers to maintaining a condition of acceptable or good oral hygiene or improving a condition such that acceptable or good hygiene results. The compositions may be provided in oral formulations such as powders, gels, pastes, tablets, capsules, gums, lozenges, mints, candy, other confectionery materials, aerosols or sprays, fluids, rinses or mouthwashes, dentifrices, such as tooth-powders, tooth-gels, tooth-pastes, and extract-impregnated dental flosses, and the like. A particularly preferred composition is a gum with a solid exterior and a liquid center, wherein both the solid exterior and the liquid center contain an effective amount of the extract composition. A particular advantage of this composition is that the liquid center delivers the extract to the oral cavity quickly thus initiating salivation, while the solid gum delivers additional extract to the oral cavity over a prolonged period, a combination that provides a particularly effective treatment.

The extract of Arialaceae, Zingiberaceae, Lamiaceae, Fabaceae, Solanaceae, Punicaceae, Asteraceae or mixtures thereof may be prepared using standard means or methods, such as by contacting the plant material with an appropriate solvent to prepare a botanical tincture, or by any other conventional means or method, such as by $CO_2$ extraction, freeze-drying, spray-drying, and the like.

One embodiment provides an herbal composition including an extract from Arialaceae, Zingiberaceae, Lamiaceae, Fabaceae, Solanaceae, Punicaceae, Asteraceae or mixtures thereof and an oral carrier in any one of a wide variety of forms; e.g., a powder, a gel, a paste, a tablet, a capsule, an oral film, a mouthwash, a gum, a candy, a confection, a lozenge, a liquid preparation such as a droplet dispenser, or aerosol dispenser, etc. In one embodiment of the invention, the tablet or capsule is disintegratable or dissolvable in the oral cavity. It is a further object of the invention to provide a method of treating an oral cavity with an herbal composition including a medicinally effective amount of an extract from the *Panax ginseng*. Further objects and advantages of the present invention will become readily apparent from a review of the following specification and claims.

Further areas of applicability of the present invention will become apparent from the detailed description provided hereinafter. It should be understood that the detailed description and specific examples, while indicating the preferred embodiment of the invention, are intended for purposes of illustration only and are not intended to limit the scope of the invention. However, the applicants reserve the right to disclaim any element or embodiment of the invention.

DETAILED DESCRIPTION

As used throughout, ranges are used as shorthand for describing each and every value that is within the range. Any value within the range can be selected as the terminus of the range.

All references cited herein are hereby incorporated by reference in their entireties.

Oral care compositions according to the present invention comprise an extract obtained from Arialaceae, Zingiberaceae, Lamiaceae, Fabaceae, Solanaceae, Punicaceae, Asteraceae or mixtures thereof. The extract is obtained from any part of the plant which includes but is not limited to the whole plant, leaves, stems, roots, fruit, seeds and seed parts.

The compositions of the invention exhibits saliva producing effect when introduced to the oral cavity.

The present invention, in various embodiments, can provide oral care compositions that increases salivation and alleviates dry mouth and the sensations of dry mouth. The oral care composition may take any dosage form useful for oral administration. Illustrative examples of these include: a dentifrice, e.g., a toothpaste, dental gel, dental cream, or tooth powder; a mouthwash, mouth rinse, or mouth spray; an oral slurry or liquid dentifrice; a gum or other confectionary; a lozenge; dental floss or dental tape; a prophylaxis paste or powder; a mono- or multi-layer oral film or gel strip, e.g., tooth strips or breath strips, preferably using a biodegradable or orally consumable film or gel; functional film or gel flakes or functional micro-, or nano-particles; a film-forming composition comprising pre-gel(s) or pre-polymer(s), e.g., film-forming dentifrices, dental paints; a tooth hardener; or a coating on an oral, e.g., orthodontic, appliance or implant.

The present invention provides oral care compositions comprising an extract of Arialaceae, Zingiberaceae, Lamiaceae, Fahaceae, Solanaceae, Punicaceae, Asteraceae or mixtures thereof.

One embodiment of an extract of Arialaceae is an extract of *Panax pseudoginseng* Wall. Var. *japonica* or *Panax ginseng*. In another embodiment of the invention the extract of Arialaceae is an extract of *Panax ginseng*.

One embodiment of an extract of Zingiberaceae is an extract of *Zingiber officinale*.

One embodiment of an extract of Lamiaceae is an extract of *Prunella vulgaris* L.

One embodiment of an extract of Fabaceae is an extract of *Glycyrrhiza echinata* L., *Glycyrrhiza uralensis* L., *Glycyrrhiza infata, Glycyrrhiza korshinskyi*, or *Glycyrrhiza uralensis*. In another embodiment of the invention, the extract of Fabaceae is an extract of *Glycyrrhiza uralensis* L.

One embodiment of an extract of Solanaceae is an extract of *Lycium chinense mill* L.

One embodiment of an extract of Punicaceae is an extract of *Punica granatum* L.

One embodiment of an extract of Asteraceae is an extract of *Spilanthes acinella* L. or *Spilanthes oleracea* L. ("*Amelia clearacea*").

Any combination of the above species can represent a mixture of the extracts. In one embodiment of the invention, the mixture includes a combination of extract of *Panax ginseng, Zingiber officinale, Prunella vulgaris* L., *Glycyrrhiza uralensis* L., *Lycium chinense mill* L., *Punica granatum* L., and *Acnzella oleracea*.

The extract of Arialaceae, Zingiberaceae, Lamiaceae, Fabaceae, Solanaceae, Punicaceae, Asteraceae or mixtures thereof may be in any form, including powder, suspension, emulsion and/or an oil. The Arialaceae, Zingiberaceae, Lamiaceae, Fabaceae, Solanaceae, Punicaceae, or Asteraceae tissue(s) used for production of any extract for use in the invention may be prepared by any means known in the art. The plant tissues processed in the above described way or in any other manner may be extracted using any suitable known extraction technique to provide an extract useful in the present invention. For example, extraction techniques that can be used include any suitable aqueous extraction or organic solvent extraction. Extraction techniques include, but are not limited to techniques which utilize water, $C_1$-$C_4$ alcohols (e.g. methanol, ethanol, propanol, butanol), ethyl acetate, acetonitrile, acetone, diethylether, dichloromethane, chloroform, tetrahydrofuran (THF) and mixtures thereof (e.g. water/methanol, methanol:THF). In one embodiment of the invention, the extreaction is an aqueous extraction with or without a cosolvent. The extraction can be conducted in a single step or in multiple steps. Any other suitable extraction technique may be used, such as steam distillation and supercritical fluid extraction.

The Asteraceae extract may be present in the oral care composition in various amounts. The Asteraceae extract is *Acmella oleracea* (para cress) extract present in an amount selected from the group consisting of greater than 0.5%; from 0.5% to 2.0%; from 0.6% to 1.50%; and 1%.

The Arialaceae, Lamiaceae or Fabaceae extract may be present in the oral care composition in various amounts. The Arialaceae, Lamiaceae or Fabaceae extract is a *Panax ginseng, Prunella vulgaris* L. or *Glycyrrhiza uralensis* L. extract and is present in an amount selected from the group consisting of from 0.05% to 1.00%; from 0.15% to 0.75%; and 0.5%.

The Punicaceae extract may be present in the oral care composition in various amounts. The Punicaceae extract is *Punica granatum* L. extract present in an amount selected from the group consisting of from 0.075% to 1.00%; from 0.08% to 0.75%; and 0.25%.

The Solanaceae extract may be present in the oral care composition in various amounts. The Solanaceae extract is *Lycium chinense mill* L. extract and is present in an amount less than 0.75%; from 0.01% to 0.10%; from 0.03% to 0.08%; and 0.05%.

The Zingiberaceae extract may be present in the oral care composition in various amounts. The Zingiberaceae extract is a *Zingiber officinale* extract present in an amount selected from the group consisting of from 0.0005% to 0.010%; from 0.001% to 0.005%; and 0.005%.

In one embodiment of the invention, the extract of Arialaceae, Zingiberaceae, Lamiaceae, Fabaceae, Solanaceae, Punicaceae, Asteraceae or mixtures thereof is further extracted with water and ethyl acetate. In a further embodiment of the invention, the water phase of the water and ethyl acetate extract is isolated and further fractionated. In a still further embodiment of the invention, the isolated water phase is fractionated via HPLC.

In another embodiment of the invention, extract of Arialaceae, Zingiberaceae, Lamiaceae, Fabaceae, Solanaceae, Punicaceae, Asteraceae or mixture the isolated water phase fractionated by HPLC is present in a concentration selected from the group consisting of 1 μg/mL-1000 μg/mL, 5 μg/mL-500 μg/mL, 8 μg/mL-120 μg/mL, 8 μg/mL-12 μg/mL; and 80 μg/mL-120 μg/mL.

The *Acmella oleracea* (para cress) extract is present in the saliva at concentrations selected from the group consisting of greater than 40 ppm; from 40 ppm to 100 ppm; from 50 ppm to 80 ppm; and 60 ppm. The concentration of the *Acmella oleracea* (para cress) extract should be measured from saliva gathered from surfaces throughout the mouth.

The *Panax ginseng, Prunella vulgaris* L. or *Glycyrrhiza uralensis* L. extract can be present in the saliva at concentrations selected from the group consisting of from 10 ppm to 50 ppm; from 17 ppm to 47 ppm; from 25 ppm to 40 ppm; and 33 ppm. The concentration of the *Panax ginseng, Prunella vulgaris* L. or *Glycyrrhiza uralensis* L. extract should be measured from saliva gathered from surfaces throughout the mouth.

The *Punica granatum* L. extract can be present in the saliva at concentrations selected from the group consisting of from 5 ppm to 50 ppm; from 5 ppm to 33 ppm; from 7 ppm to 33 ppm; and from 10 ppm to 25 ppm; and preferably 17 ppm. The concentration of the *Punica granatum* L. extract should be measured from saliva gathered from surfaces throughout the mouth.

The *Zingiber officinale* extract can be present in the saliva at concentrations selected from the group consisting of from 0.1 ppm to 2 ppm; from 0.2 ppm to 1.7 ppm; from 0.2 ppm to 0.7 ppm; and 0.3 ppm. The concentration of the *Zingiber officinale* extract should be measured from saliva gathered from surfaces throughout the mouth.

The *Lycium chinense mill* L. extract can be present in the saliva at concentrations selected from the group consisting of less than 5 ppm; from 1.7 ppm to 5 ppm; from 2.5 ppm to 4 ppm; and 3.3 ppm. The concentration of the *Lycium chinense mill* L. extract should be measured from saliva gathered from surfaces throughout the mouth.

Another embodiment of the invention generally relates to 1) compositions that are used orally in treating the clinical condition known as xerostomia, that increase salivation, alleviate dry mouth and the sensations of dry mouth, and thereby aid in maintaining or improving oral hygiene, and methods of using same; 2) compositions that may be described as oral sensates, that produce sensations of tingling, numbness, moistness and other sensations, and methods of using same; 3) as a flavor enhancer and potentiator; 4) compositions that may include any potential combinations of effects as described above in 1, 2, and 3, and methods of using same.

Saliva extract content is defined as results obtained by the following methodology. Whole mouth unstimulated saliva was collected from subjects treated with either extract containing mouthrinse or placebo in a double blind clinical study. The samples were harvested into preweighed 1.5 mL vials and the weight of the sample determined by reweighing the vial immediately after collection. Samples were collected from the subjects at time periods selected from the group consisting of 2 minutes, 30 minutes 1 hour, 2 hours and 5 hours, 6 and 12 hours after rinsing. For each data point, samples were also collected prior to the administration of sample to obtain baseline levels. No eating or drinking was permitted prior to collection of the 2 hour samples. For 6 hour samples, subjects were allowed to eat and drink as desired between two and six hours following brushing. Twelve hour samples were collected after an overnight period during which subjects were directed to drink liquids as desired, but to refrain from eating. The use of chewing gum, hard candy, and lozenges was not permitted for any time point.

Samples, collected as specified, should be tested using Liquid Chromatography-Mass Spectrometry to determine the quantity of one or more identifiable compounds found in an original extract. This value is used to calculate on a pro rata basis the saliva extract content level in the saliva.

For the extract of Arialaceae, samples may also be collected from the subjects at 2 minutes, 15 minutes, 2 hours, 6 hours and 12 hours after rinsing for testing of saliva content. It is advantageous to have the saliva content of these time frames within the range of from 10 ppm to 50 ppm; preferably from 17 ppm to 47 ppm; preferably from 25 ppm to 40 ppm; and preferably 33 ppm.

For the extract of Zingiberaceae, samples may also be collected from the subjects at 2 minutes, 30 minutes 1 hour, 2 hours and 5 hours, 6 and 12 hours after rinsing for testing of saliva content. It is advantageous to have the saliva content of these time frames within the range of preferably from 0.1 ppm to 2 ppm; preferably from 0.2 ppm to 1.7 ppm; preferably from 0.2 ppm to 0.7 ppm; and preferably 0.3 ppm.

For the extract of Lamiaceae, samples may also be collected from the subjects at 2 minutes, 30 minutes 1 hour, 2 hours and 5 hours, 6 and 12 hours after rinsing for testing of saliva content. It is advantageous to have the saliva content of these time frames within the range of preferably from 10 ppm to 50 ppm; preferably from 17 ppm to 40 ppm; and preferably 33 ppm.

For the extract of Fabaceae, samples may also be collected from the subjects at 2 minutes, 30 minutes 1 hour, 2 hours and 5 hours, 6 and 12 hours after rinsing for testing of saliva content. It is advantageous to have the saliva content of these time frames within the range of from 10 ppm to 50 ppm; preferably from 17 ppm to 47 ppm; preferably from 25 ppm to 40 ppm; and preferably 33 ppm.

For the extract of Solanaceae, samples may also be collected from the subjects at 2 minutes, 30 minutes 1 hour, 2 hours and 5 hours, 6 and 12 hours after rinsing for testing of saliva content. It is advantageous to have the saliva content of these time frames within the range of preferably from 1.7 ppm to 5 ppm; preferably from 2.5 ppm to 4 ppm; and preferably 3.3 ppm.

For the extract of Punicaceae, samples may also be collected from the subjects at 2 minutes, 30 minutes 1 hour, 2 hours and 5 hours, 6 and 12 hours after rinsing for testing of saliva content. It is advantageous to have the saliva content of these time frames within the range of preferably from 5 ppm to 50 ppm; preferably from 5 ppm to 33 ppm; preferably from 7 ppm to 33 ppm; preferably from 10 ppm to 25 ppm; and preferably 17 ppm.

For the extract of Asteraceae, samples may also be collected from the subjects at 2 minutes, 30 minutes 1 hour, 2 hours and 5 hours, 6 and 12 hours after rinsing for testing of saliva content. It is advantageous to have the saliva content of these time frames within the range of preferably from 40 ppm to 100 ppm; preferably from 50 ppm to 80 ppm; and preferably 60 ppm.

In one embodiment of the oral care composition, the composition results in 50%-150% of the % increase in RFU (relative fluorescence unit) in a calcium mobilization assay for determining agonist activity of the human M3 receptor relative to the $EC_{50}$ of acetylcholine (e.g. if the $EC_{50}$ of acetylcholine results in a 100% increase in RFU, then the oral care composition of the invention should show a 50%-150% increase in RFU); in an alternative embodiment of this oral care composition, the composition results in 60%-125% of the % increase in RFU relative to the $EC_{50}$ of acetylcholine; in a further alternative embodiment of this oral care composition, the composition results in 75%-110% of the % increase in RFU relative to the $EC_{50}$ of acetylcholine.

While not wishing to be bound by theory, the residual water phase fractions enrich one or more oligosaccharides (oligosaccharide being defined as a carbohydrate containing from two to ten saccharides linked together). Within the context of this invention, the term oligosaccharide is not intended to encompass glycosidic forms, e.g. a saponin which may have an oligosaccharide covalently bonded to an aglycone. In one embodiment of the invention, the oligosaccharide is di-, tri- or tetra-saccharide. In another embodiment of the invention, the oligosaccharide is a tetrasaccharide comprising a dimer of disaccharides.

In another embodiment of the oral care composition, the composition contains not more than 0.01% acetylcholine, pilocarpine, muscarine, arecoline, carbachol or bethanecol. In alternative embodiment of this oral care composition, the composition contains not more than 0.001% acetylcholine, pilocarpine, muscarine, arecoline, carbachol or bethanecol. In alternative embodiment of this oral care composition, the composition contains not more than 0.0001% acetylcholine, pilocarpine, muscarine, arecoline, carbachol or bethanecol. In alternative embodiment of this oral care composition, the composition contains no (0%) acetylcholine, pilocarpine, muscarine, arecoline, carbachol or bethanecol.

The oral care composition can, and preferably will, also include one or more solubilizing agents to solubilize the extract of Arialaceae, Zingiberaceae, Lamiaceae, Fabaceae, Solanaceae, Punicaceae, Asteraceae or mixtures thereof. The solubilizing agent can be any solubilizing agent that is effective to solubilize the extract of Arialaceae, Zingiberaceae, Lamiaceae, Fabaceae, Solanaceae, Punicaceae, Asteraceae or mixtures thereof. For example, in various embodiments the solubilizing agent can be at least one of an orally acceptable surfactant, flavoring oil, alcohol, and solubilizing humectant (e.g., propylene glycol).

Examples of surfactants that can be used include anionic, nonionic, amphoteric, zwitterionic, and cationic.

The oral care compositions comprise an orally acceptable vehicle. Any suitable orally acceptable vehicle can be used, such as those described in U.S. Pat. No. 4,894,220 titled "Antibacterial Anti-Plaque Oral Composition," which is incorporated by reference herein. For example, the vehicle can include a water-phase with humectant. In the present invention, the water and humectant liquid phase can comprise at least 10% by weight of the oral care composition. Moreover, preferably the humectant comprises propylene glycol, which can help to solubilize the Ginseng extract. The remainder of the humectant is preferably glycerine and/or sorbitol and/or xylitol. Water is present typically in amount of at least 3% by weight; and glycerine and/or sorbitol and/or xylitol typically total 6.5% to 75% by weight of the oral preparation, more typically 10% to 75%, and, together with the solubilizing humectant, the essential humectant components typically amount to 7% to 80% by weight of the oral preparation. Reference hereto to sorbitol refers to the material typically as available commercially in 70% aqueous solutions. Where the composition contains a substantially water insoluble noncationic anti-bacterial agent, the composition will preferably be free of at least significant amounts of polyethylene glycol, particularly of average molecular weight of 600 or more, since polyethylene glycol can inhibit the antibacterial activity of a noncationic antibacterial agent, even when another component, such as, propylene glycol is present to effect its solubilization.

In one embodiment of the invention, the vehicle is alcohol free. Optionally, the vehicle may be fluoride free. In another embodiment of the invention, the vehicle can also be a water-alcohol mixture. Generally, the weight ratio of water to alcohol is in the range of from 1:1 to 20:1, preferably 3:1 to 10:1 and more preferably 4:1 to 6:1. The total amount of water-alcohol mixture in, for example, a mouthwash is typically in the range of from 70 to 99.9% by weight. The alcohol is a non-toxic alcohol such as ethanol or isopropanol.

In one embodiment of the invention, the oral care composition of the invention is topically delivered to the oral cavity. In another embodiment of the invention the dry mouth alleviating components of the invention does not provide a systemic effect.

A humectant, such as glycerine, sorbitol, xylitol, propylene glycol, ethanol and mixtures thereof may be present in an amount of 10 to 30% by weight. The oral care composition may contain water at 5% to 30% by weight. Liquid dentifrices typically contain 50% to 85% of water, may contain 0.5% to 20% by weight of non-toxic alcohol and may also contain 10% to 40% by weight of humectant, such as glycerine, sorbitol, and/or xylitol. Sorbitol refers to the material typically available commercially in 70% aqueous solutions. Ethanol is the preferred non-toxic alcohol. The alcohol assists in dissolving the extract of Arialaceae, Zingiberaceae, Lamiaceae, Fabaceae, Solanaceae, Punicaceae, Asteraceae or mixtures thereof and the water-insoluble non-cationic anti-bacterial agent.

It may be desirable to include within the dentifrice composition one or more therapeutic agents that prevent, treat and/or reduce the symptoms related to various oral or systemic diseases or conditions. Useful therapeutic agents include all those known or developed in the art including steroids, NSAIDs, a fluoride ion source, polycarboxylate polymers, polyvinyl methyl ether/maleic anhydride (PVME/MA) copolymers, an arginine ester, a zinc ion source, a stannous ion source, delmopinol, tartar control agents, an antibacterial agent, triclosan and salts thereof, chlorhexidine, alexidine, hexetidine, sanguinarine, benzalkonium chloride, salicylanilide, domiphen bromide, cetylpyridinium chloride (CPC), tetradecylpyridinium chloride (TPC), N-tetradecyl-4-ethylpyridinium chloride (TDEPC), octenidine, octapinol, nisin, a zinc ion source, a copper ion source, an essential oil, a furanone, anti-inflammatory agents, anti-plaque agents, antioxidants, and a bacteriocins, and salts thereof, honokiol, vitamins, anti-attachment agents, proteinaceous agents, peptides. A further illustrative list of useful antibacterial agents is provided in U.S. Pat. No. 5,776,435, the contents of which are incorporated herein by reference.

Some embodiments of the invention provide oral care compositions which further comprise a fluoride ion source which includes but is not limited to stannous fluoride, sodium fluoride, potassium fluoride, amine fluoride, ammonium fluoride, stannous monofluorophosphate, sodium monofluorophosphate, potassium monofluorophosphate, amine monofluorophosphate, ammonium monofluorophosphate, stannous fluorosilicate, sodium fluorosilicate, potassium fluorosilicate, amine fluorosilicate ammonium fluorosilicate, and mixtures thereof.

Abrasives may be added to the dentifrice formulation if desired. Any suitable oral care abrasive or polishing agent may be used. Abrasives such as silica, calcined alumina, sodium bicarbonate, calcium carbonate, dicalcium phosphate and calcium pyrophosphate may be included in the base dentifrice compositions used in the practice of the present invention. An embodiment of the abrasives include, but are not limited to, silica abrasives such as precipitated silicas, sodium metaphosphate, potassium metaphosphate, tricalcium phosphate, dihydrated dicalcium phosphate, aluminum silicate, calcined alumina, bentonite or other siliceous materials, particulate thermosetting resins, such as melamine, phenolic, and urea-formaldehydes, and cross-linked polyepoxides and polyesters.

Visually clear dentifrice compositions may be obtained by using an abrasive such as collodial silica, e.g., those sold under the trade designation Zeodent 115 available from the Huber Corporation or alkali metal aluminosilicate complexes (that is, silica containing alumina combined in its matrix) which have refractive indices close to the refractive indices of gelling agent-liquid (including water and/or humectant) systems used in dentifrice compositions.

As desired, any other additives may be included in the dentifrice composition for reasons of e.g., manufacturing, stability, aesthetics, therapeutic effect, consumer appeal, etc. Exemplary additives include all other conventional dentifrice additives, viscosity modifiers, diluents, foam modulators, saliva stimulating agents, desensitizing agents, whitening agents, enzymes, pH modifying agents, mouth-feel agents, sweeteners, colorants, opacifiers, and breath freshening agents. Exemplary additives include, but are not limited to those agents cited in the International Cosmetic Ingredient Dictionary and Handbook, 14$^{th}$ Edition (2012), which is incorporated herein by reference.

One embodiment of the invention is for the oral care composition to further comprise other agents for increasing salivation, alleviating dry mouth or the sensations of dry mouth which are not the described extracts of Arialaceae, Zingiberaceae, Lamiaceae, Fabaceae, Solanaceae, Punicaceae, Asteraceae or mixtures thereof. Examples of such agents include, but are not limited to, food acids such as citric, lactic, malic, succinic, ascorbic, adipic, fumaric, and tartaric acids, and mixtures thereof. One or more saliva stimulating agents are optionally present in a saliva stimulating effective total amount.

Another embodiment of the invention is that other saliva inducing compounds such as citric acid and/or other extracts besides the extracts of Arialaceae, Zingiberaceae, Lamiaceae, Fabaceae, Solanaceae, Pzmicaceae, Asteraceae or mixtures thereof are not present in the oral care composition.

The present invention provides for methods and processes of using the oral care compositions of the present invention to treat and inhibit oral conditions, such as oral inflammatory conditions, dental plaque deposits on the teeth and oral tissues, and dental calculus. Further, the oral care compositions can serve as antioxidants. The present invention provides for commercial packaging for the oral care compositions to distribute and store the oral care compositions.

The present invention also provides for the use of the composition of described in the specification or claims in the manufacture of a medicament for the treatment of dry mouth.

The oral care compositions can be applied to the subject in any suitable manner, as is known in the art. For example, the oral care compositions can be applied to the subject's oral cavity using a suitable applicator or delivery device, such as a brush, dental strip, film, syringe, tape, gum, pill, or any other applicator or delivery device that is known in the art. The compositions can be used in prophylactic methods and processes to promote and maintain oral health, appearance, and breath freshness. The oral care compositions can be repeatedly applied to the subject over a number of days according to a particular treatment schedule to treat and/or inhibit dental plaque deposits, dental calculus deposits, and oral inflammatory conditions and to provide anti-oxidant activity. Instructions setting forth the treatment schedule can be provided with the commercial packaging.

The present invention is further illustrated through the following non-limiting examples.

EXAMPLES

Example 1

Human recombinant CHO-K1 cells expressing the human M3 muscarinic receptor were used in an assay as an in vitro model test of an extract of Arialaceae, Zingiberaceae, Lamiaceae, Fabaceae, Solanaceae, Punicaceae, Asteraceae or mixtures thereof effect in increasing salivation. Pilocarpine was used as reference agonist. 10 µM of calcium ionophore was added to plate wells to normalize total cell calcium to agonist response. The cells were grown to confluence in the plate wells. The cells were then washed, fluorescent dye was added in assay buffer and equilibrated before analysis. The extract from *Panax ginseng, Zingiber officinale, Prunella vulgaris* L., *Glycyrrhiza uralensis* L., *Lycium chinense mill* L., *Punica granatum* L., and *Acmella oleracea* was introduced to the plate wells and then activity was visualized with fluorescence at 485 nm excitation and 525 nm emission. Points were collected every 2 seconds for at least 60 seconds. The maximum peak height was recorded, which occurred at 15 seconds. Pilocarpine was also tested in the same way as the extract from *Panax ginseng, Zingiber officinale, Prunella vulgaris* L., *Glycyrrhiza uralensis* L., *Lycium chinense mill* L., *Punica granatum* L., and *Acmella oleracea* so as to compare the extract's efficacy with Pilocarpine. The data presented in Tables 1A-1G below show the response of the cells against an extract from *Panax ginseng, Zingiber officinale, Prunella vulgaris* L., *Glycyrrhiza uralensis* L., *Lycium chinense mill* L., *Punica granalum* L., and *Acmella oleracea* compared to Pilocarpine.

TABLE 1A

| Concentration of *Panax ginseng* Powder Extract, ppm | % Response of Pilocarpine |
|---|---|
| 100 | 72 |
| 500 | 123 |
| 1000 | 52 |

*Panax ginseng* extract obtained from the root (radix) via a water and ethanol extraction (from Cactus Botanics Ltd.).

TABLE 1B

| Concentration of *Zingiber officianale* Extract, ppm | % Response of Pilocarpine |
|---|---|
| 5 | 106 |
| 50 | 58 |
| 100 | 81 |
| 500 | 80 |
| 1000 | 73 |

*Zingiber officianale* extract obtained from the root (radix) via a water extraction (from Cactus Botanics Ltd.).

TABLE 1C

| Concentration of *Prunella vulgaris* L. Powder Extract, ppm | % Response of Pilocarpine |
|---|---|
| 100 | 48 |
| 500 | 115 |
| 1000 | 79 |

*Prunella vulgaris* extract obtained from the whole grass (*Spica Prunellae*) via a water extraction (from Cactus Botanics Ltd.).

TABLE 1D

| Concentration of *Glcyrrhiza uralensis* L. Powder 22% Extract, ppm | % Response of Pilocarpine |
|---|---|
| 100 | 49 |
| 500 | 82 |
| 1000 | 44 |

*Glycyrrhiza uralensis* extract obtained from the root (radix) via a water extraction (from DH Nutraceuticals, LLC).

TABLE 1E

| Concentration of *Lycium chinense* mill L. 40% Extract, ppm | % Response of Pilocarpine |
|---|---|
| 5 | 190 |
| 50 | 600 |
| 100 | 67 |
| 500 | 79 |
| 1000 | 89 |

*Lycium chinense* mill extract obtained from the fruit via a water extraction (from Amax NutraSource, Inc.).

TABLE 1F

| Concentration of *Punica granatum* L. Extract, ppm | % Response of Pilocarpine |
|---|---|
| 5 | 30 |
| 50 | 51 |
| 100 | 99 |
| 500 | 102 |
| 1000 | 42 |

*Punica granatum* extract obtained from the hull via a water and ethanol extraction (from Cactus Botanics Ltd.).

TABLE 1G

| Concentration of *Acmella oleracea* (Para cress) Powder Extract, ppm | % Response of Pilocarpine |
|---|---|
| 100 | −11 |
| 500 | 115 |
| 1000 | 411 |

*Acmella oleracea* extract obtained from Cosmetochem International AG.

The use in vitro of *Acmella oleracea* extract at 1000 ppm, *Panax ginseng* extract or *Glycyrrhiza uralensis* L. extract at 500 ppm, *Punica granatum* L. extract at between 100 and 500 ppm, *Lycium chinense mill* L. extract at 50 ppm, *Zingiber officinale* extract at 5 ppm, showed increases in the inducement of saliva production.

Example 2

A liquid composition is prepared that is delivered to the oral cavity as a rinse or a spray. Compositions A, B, C, D, E and F described herein, are examples of liquid compositions. In Tables 2A-2G, each of the components of A, B, C, D, E and F are listed along with the approximate amount of each component in weight percent (%) relative to the overall composition.

TABLE 2A

| Ingredients | A | B | C | D | E | F |
|---|---|---|---|---|---|---|
| Water | 69.85% | 69.50% | 69.25% | 69.85% | 69.50% | 69.25% |
| Glycerin | 10% | 10% | 10% | 20% | 20% | 20% |
| Propylene Glycol | 10% | 10% | 10% | 0% | 0% | 0% |
| Sorbitol | 10% | 10% | 10% | 10% | 10% | 10% |
| *Panax ginseng* extract | 0.15% | 0.50% | 0.75% | 0.15% | 0.50% | 0.75% |
| | 100.0% | 100.0% | 100.0% | 100.0% | 100.0% | 100.0% |

TABLE 2B

| Ingredients | A | B | C | D | E | F |
|---|---|---|---|---|---|---|
| Water | 69.999% | 69.995% | 69.975% | 69.999% | 69.995% | 69.975% |
| Glycerin | 10% | 10% | 10% | 20% | 20% | 20% |
| Propylene Glycol | 10% | 10% | 10% | 0% | 0% | 0% |
| Sorbitol | 10% | 10% | 10% | 10% | 10% | 10% |
| *Zingiber officinale* extract | 0.001% | 0.005% | 0.025% | 0.001% | 0.005% | 0.025% |
| | 100.0% | 100.0% | 100.0% | 100.0% | 100.0% | 100.0% |

TABLE 2C

| Ingredients | A | B | C | D | E | F |
|---|---|---|---|---|---|---|
| Water | 69.85% | 69.50% | 69.25% | 69.85% | 69.50% | 69.25% |
| Glycerin | 10% | 10% | 10% | 20% | 20% | 20% |
| Propylene Glycol | 10% | 10% | 10% | 0% | 0% | 0% |
| Sorbitol | 10% | 10% | 10% | 10% | 10% | 10% |
| *Prunella vulgaris* L. extract | 0.15% | 0.50% | 0.75% | 0.15% | 0.50% | 0.75% |
| | 100.0% | 100.0% | 100.0% | 100.0% | 100.0% | 100.0% |

TABLE 2D

| Ingredients | A | B | C | D | E | F |
|---|---|---|---|---|---|---|
| Water | 69.85% | 69.50% | 69.25% | 69.85% | 69.50% | 69.25% |
| Glycerin | 10% | 10% | 10% | 20% | 20% | 20% |
| Propylene Glycol | 10% | 10% | 10% | 0% | 0% | 0% |
| Sorbitol | 10% | 10% | 10% | 10% | 10% | 10% |
| *Glycyrrhiza uralensis* L. extract | 0.15% | 0.50% | 0.75% | 0.15% | 0.50% | 0.75% |
| | 100.0% | 100.0% | 100.0% | 100.0% | 100.0% | 100.0% |

TABLE 2E

| Ingredients | A | B | C | D | E | F |
|---|---|---|---|---|---|---|
| Water | 72.975% | 72.95% | 72.92% | 67.97% | 67.95% | 67.92% |
| Glycerin | 10% | 10% | 10% | 15% | 15% | 15% |
| Propylene Glycol | 7% | 7% | 7% | 7% | 7% | 7% |
| Sorbitol | 10% | 10% | 10% | 10% | 10% | 10% |
| *Lycium chinense mill* L. extract | 0.03% | 0.05% | 0.08% | 0.03% | 0.05% | 0.08% |
| | 100.0% | 100.0% | 100.0% | 100.0% | 100.0% | 100.0% |

TABLE 2F

| Ingredients | A | B | C | D | E | F |
|---|---|---|---|---|---|---|
| Water | 72.92% | 72.50% | 72.25% | 67.92% | 67.50% | 67.25% |
| Glycerin | 10% | 10% | 10% | 15% | 15% | 15% |
| Propylene Glycol | 7% | 7% | 7% | 7% | 7% | 7% |
| Sorbitol | 10% | 10% | 10% | 10% | 10% | 10% |
| *Punica granatum* L. extract | 0.08% | 0.50% | 0.75% | 0.08% | 0.50% | 0.75% |
| | 100.0% | 100.0% | 100.0% | 100.0% | 100.0% | 100.0% |

TABLE 2G

| Ingredients | A | B | C | D | E | F |
|---|---|---|---|---|---|---|
| Water | 72.40% | 72.00% | 71.50% | 67.40% | 67.00% | 66.50% |
| Glycerin | 10% | 10% | 10% | 15% | 15% | 15% |
| Propylene Glycol | 7% | 7% | 7% | 7% | 7% | 7% |
| Sorbitol | 10% | 10% | 10% | 10% | 10% | 10% |
| *Acmella oleracea* (para cress) extract | 0.60% | 1.00% | 1.50% | 0.60% | 1.00% | 1.50% |
| | 100.0% | 100.0% | 100.0% | 100.0% | 100.0% | 100.0% |

Compositions A, B, C, D, E and F are prepared by combining components, such that any solid components are substantially dissolved. Any appropriate mixing means and methods may be used to facilitate the combining, dissolving or dispersing of the components to produce the liquid composition. Once prepared, the composition may be delivered to the oral cavity as a rinse or as an aerosol or spray, in any conventional manner. Compositions A, B, C, D, E and F are particularly effective in alleviating dry mouth.

Example 3

A gel or paste composition may be prepared that is delivered to the oral cavity as a toothpaste. Compositions G, H, I, J, K and L, described herein, are examples of paste and gel compositions. In Tables 3A-3G, each of the components of G, H, I, J, K and L are listed along with the approximate amount of each component in weight percent (%) relative to the overall composition.

TABLE 3A

| Ingredients | G | H | I | J | K | L |
|---|---|---|---|---|---|---|
| Water | 38.11% | 37.76% | 37.51% | 33.35% | 33.00% | 32.75% |
| Glycerin | 10.0% | 10.0% | 15.0% | 15.0% | 20.0% | 20.0% |
| Carboxymethyl cellulose | 0.5% | 0.5% | 0.5% | 0.5% | 0.5% | 0.5% |
| Humectant | 20% | 20% | 20% | 25% | 25% | 25% |
| Silica | 30% | 30% | 25% | 25% | 20% | 20% |
| Saccharin | 1% | 1% | 1% | 1% | 1% | 1% |
| Sodium Fluoride | 0.24% | 0.24% | 0.24% | 0.00% | 0.00% | 0.00% |
| *Panax ginseng* extract | 0.15% | 0.50% | 0.75% | 0.15% | 0.50% | 0.75% |
| | 100.0% | 100.0% | 100.0% | 100.0% | 100.0% | 100.0% |

TABLE 3B

| Ingredients | G | H | I | J | K | L |
|---|---|---|---|---|---|---|
| Water | 38.26% | 38.25% | 38.23% | 33.50% | 33.50% | 33.48% |
| Glycerin | 10.0% | 10.0% | 15.0% | 15.0% | 20.0% | 20.0% |
| Carboxymethyl cellulose | 0.5% | 0.5% | 0.5% | 0.5% | 0.5% | 0.5% |
| Humectant | 20% | 20% | 20% | 25% | 25% | 25% |
| Silica | 30% | 30% | 25% | 25% | 20% | 20% |
| Saccharin | 1% | 1% | 1% | 1% | 1% | 1% |
| Sodium Fluoride | 0.24% | 0.24% | 0.24% | 0.00% | 0.00% | 0.00% |
| *Zingiber officinale* extract | 0.001% | 0.005% | 0.025% | 0.001% | 0.005% | 0.025% |
|  | 100.0% | 100.0% | 100.0% | 100.0% | 100.0% | 100.0% |

TABLE 3C

| Ingredients | G | H | I | J | K | L |
|---|---|---|---|---|---|---|
| Water | 38.11% | 37.76% | 37.51% | 33.35% | 33.00% | 32.75% |
| Glycerin | 10.0% | 10.0% | 15.0% | 15.0% | 20.0% | 20.0% |
| Carboxymethyl cellulose | 0.5% | 0.5% | 0.5% | 0.5% | 0.5% | 0.5% |
| Humectant | 20% | 20% | 20% | 25% | 25% | 25% |
| Silica | 30% | 30% | 25% | 25% | 20% | 20% |
| Saccharin | 1% | 1% | 1% | 1% | 1% | 1% |
| Sodium Fluoride | 0.24% | 0.24% | 0.24% | 0.00% | 0.00% | 0.00% |
| *Prunella vulgaris* L. extract | 0.15% | 0.50% | 0.75% | 0.15% | 0.50% | 0.75% |
|  | 100.0% | 100.0% | 100.0% | 100.0% | 100.0% | 100.0% |

TABLE 3D

| Ingredients | G | H | I | J | K | L |
|---|---|---|---|---|---|---|
| Water | 38.23% | 33.21% | 38.18% | 33.48% | 38.45% | 33.43% |
| Glycerin | 10.0% | 10.0% | 15.0% | 15.0% | 20.0% | 20.0% |
| Carboxymethyl cellulose | 0.5% | 0.5% | 0.5% | 0.5% | 0.5% | 0.5% |
| Humectant | 20% | 25% | 20% | 25% | 20% | 25% |
| Silica | 30% | 30% | 25% | 25% | 20% | 20% |
| Saccharin | 1% | 1% | 1% | 1% | 1% | 1% |
| Sodium Fluoride | 0.24% | 0.24% | 0.24% | 0.00% | 0.00% | 0.00% |
| *Glycyrrhiza uralensis* L. extract | 0.03% | 0.05% | 0.08% | 0.03% | 0.05% | 0.08% |
|  | 100.0% | 100.0% | 100.0% | 100.0% | 100.0% | 100.0% |

TABLE 3E

| Ingredients | G | H | I | J | K | L |
|---|---|---|---|---|---|---|
| Water | 38.23% | 33.21% | 38.18% | 33.48% | 38.45% | 33.43% |
| Glycerin | 10.0% | 10.0% | 15.0% | 15.0% | 20.0% | 20.0% |
| Carboxymethyl cellulose | 0.5% | 0.5% | 0.5% | 0.5% | 0.5% | 0.5% |
| Humectant | 20% | 25% | 20% | 25% | 20% | 25% |
| Silica | 30% | 30% | 25% | 25% | 20% | 20% |
| Saccharin | 1% | 1% | 1% | 1% | 1% | 1% |
| Sodium Fluoride | 0.24% | 0.24% | 0.24% | 0.00% | 0.00% | 0.00% |
| *Lycium granatum* L. extract | 0.03% | 0.05% | 0.08% | 0.03% | 0.05% | 0.08% |
|  | 100.0% | 100.0% | 100.0% | 100.0% | 100.0% | 100.0% |

TABLE 3F

| Ingredients | G | H | I | J | K | L |
|---|---|---|---|---|---|---|
| Water | 38.18% | 32.76% | 37.51% | 33.43% | 38.00% | 32.75% |
| Glycerin | 10.0% | 10.0% | 15.0% | 15.0% | 20.0% | 20.0% |
| Carboxymethyl cellulose | 0.5% | 0.5% | 0.5% | 0.5% | 0.5% | 0.5% |
| Humectant | 20% | 25% | 20% | 25% | 20% | 25% |
| Silica | 30% | 30% | 25% | 25% | 20% | 20% |
| Saccharin | 1% | 1% | 1% | 1% | 1% | 1% |
| Sodium Fluoride | 0.24% | 0.24% | 0.24% | 0.00% | 0.00% | 0.00% |
| *Punica granatum* L. extract | 0.08% | 0.50% | 0.75% | 0.08% | 0.50% | 0.75% |
| | 100.0% | 100.0% | 100.0% | 100.0% | 100.0% | 100.0% |

TABLE 3G

| Ingredients | G | H | I | J | K | L |
|---|---|---|---|---|---|---|
| Water | 37.66% | 32.26% | 36.76% | 32.90% | 37.50% | 32.00% |
| Glycerin | 10.0% | 10.0% | 15.0% | 15.0% | 20.0% | 20.0% |
| Carboxymethyl cellulose | 0.5% | 0.5% | 0.5% | 0.5% | 0.5% | 0.5% |
| Humectant | 20% | 25% | 20% | 25% | 20% | 25% |
| Silica | 30% | 30% | 25% | 25% | 20% | 20% |
| Saccharin | 1% | 1% | 1% | 1% | 1% | 1% |
| Sodium Fluoride | 0.24% | 0.24% | 0.24% | 0.00% | 0.00% | 0.00% |
| *Acmella oleracea* (para cress) extract | 0.60% | 1.00% | 1.50% | 0.60% | 1.00% | 1.50% |
| | 100.0% | 100.0% | 100.0% | 100.0% | 100.0% | 100.0% |

Alternatively, each of the formulations in Tables 3A-3G may be free of fluoride by removing the fluoride source and substituting with water.

Compositions G, H, I, J, K and L are prepared by combining components. Any appropriate mixing means and methods may be used to facilitate the combining, dissolving, or dispersing of the components to produce the liquid composition. Once prepared, the composition may be delivered to the oral cavity as a toothpaste composition, in any conventional manner. Compositions G, H, I, J, K and L are particularly effective in alleviating dry mouth.

Example 4

Mouthrinse compositions are prepared in accordance with this invention and are delivered to the oral cavity of subjects who subsequently rinse. Unstimulated saliva is collected from the subjects treated with the compositions at 2 hours after rinsing. The samples are harvested into preweighed 1.5 mL vials and the weight of the sample is determined by reweighing the vial immediately after collection. For each data point, samples are also collected prior to the administration of compositions to obtain baseline levels. No eating or drinking is permitted prior to collection of the samples. Samples are tested using Liquid Chromatography-Mass Spectrometry to determine the quantity of one or more identifiable compounds found in an original extract. This value is used to calculate on a pro rata basis the saliva extract content level in the saliva. The saliva extract content of the subjects falls within the range of from 10 ppm to 50 ppm. The subjects having these saliva contents have alleviated dry mouth.

Example 5

54.0 grams of *Panax ginseng* extract described above was dissolved/suspended in 150 mL of water and subsequently extracted with ethyl acetate by liquid/liquid separation (3×150 mL ethyl acetate). The combined organic ethyl acetate phases were evaporated under reduced pressure to dryness (yield: 1615.3 mg (1.6153 g)) while the residual water phase was lyophilized (yield: 50,902.0 mg (50.9020 g)).

1.4 g of the dried ethyl acetate phase was separated by MPLC on reverse phase material via gradient elution (e.g. use of water/acetonitrile) and fractionation determined by UV absorption of the compounds in the extract to produce 15 separate fractions. Each fraction is dried via vacuum evaporation and aliquots prepared for M3 receptor assay testing.

500 mg of the lyophilized residual water phase was separated using a normal phase silica HPLC column using a gradient from an acetonitrile/water mixture owing to the relatively high polarity of the compounds in the extract. 10 fractions were obtained utilizing this method and analyzed by HPLC-UV-ELSD (ELSD—Evaporative Light Scattering Detector). Each fraction is dried via vacuum evaporation and aliquots prepared for M3 receptor assay testing.

57.0 grams of *Zingiber officinalis* extract described above was dissolved/suspended in 150 mL of water and subsequently extracted with ethyl acetate by liquid/liquid separation (3×150 mL ethyl acetate). The combined organic ethyl acetate phases were evaporated under reduced pressure to dryness (yield: 498.4 mg (0.4984 g)) while the residual water phase was lyophilized (yield: 46,176.9 mg (46.1769 g)).

300 mg of the dried ethyl acetate phase was separated via preparative reverse phase HPLC via gradient elution (e.g. use of water/acetonitrile) and fractionation determined by UV absorption of the compounds in the extract to produce 15 separate fractions. Each fraction is dried via vacuum evaporation and aliquots prepared for M3 receptor assay testing.

500 mg of the lyophilized residual water phase was separated using a normal phase silica HPLC column using a gradient from an acetonitrile/water mixture owing to the relatively high polarity of the compounds in the extract. 10 fractions were obtained utilizing this method and analyzed by HPLC-UV-ELSD. Each fraction is dried via vacuum evaporation and aliquots prepared for M3 receptor assay testing.

Example 6

The extracts of the invention were tested on the human M3 receptor in agonist mode using the calcium mobilization ($Ca^{2+}$) assay:
Cells: Mammalian cells CHO-K1 expressing the human M3 receptor
Control aginist: Acetylcholine (Sigma, Catalog No. A9101)
Calcium assay kit: Screen Quest™ Fluo-8 No Wash kit (AAT Bioquest, Catalog No. 36315)
Tested conc.: 10 μg and 100 μg
CHO-K1 cells expressing M3 receptor were seeded in 384-well plates and cultured overnight. The $Ca^{2+}$ flux assay was conducted according to the manufacturer's protocol. Calcium dye-containing buffer (Hankss' buffer with 20 mM HEPES) was added to the cells and incubated for 60 minutes at 37° C. Calcium flux was monitored for 90 seconds with compounds injected into the wells at $19^{th}$ second. 1% DMSO final was present in all reactions. Data measurements made as % increase in Relative Fluorescence Units (RFU).

A. *Panax ginseng* Extract and Residual Water Phase Fractions

*Panax ginseng* extract as obtained from Cactus Botanics Ltd. displayed greater % increase in RFU at a concentration of 100 μg/mL when compared to the $EC_{50}$ concentration of acetylcholine. Lower concentrations of *Panax ginseng* extract (i.e. 10 μg/mL) still result in about 75% of the % increase in RFU when compared to the $EC_{50}$ concentration of acetylcholine.

The residual water phase fractions of *Panax ginseng* extract displayed at least 200% increase in RFU (which is over 60% of the increase by the $EC_{50}$ concentration of acetylcholine) and surprisingly showed greater % increase in RFU when less concentrated fractions were tested (i.e. 10 μg/mL generally had greater % increase in RFU than 100 μg/mL) especially for the first five fractions.

While not wishing to be bound by theory, the residual water phase fractions enrich one or more of the ginsenosides which correlate with the following M.W. associated with the detected mass spectra peaks:

766.487 (ginsenoside Rg5, (20E)-ginsenoside F4, ginsenoside F4, ginsenoside Rg6)
784.497 (ginsenoside C, (20R)-ginsenoside Rg3, (20R)-ginsenoside Rg2)
800.492 (ginsenoside Rf, ginsenoside Ia, ginsenoside Ib, ginsenoside A2)
962.545 (ginsensoside M6a, ginsenoside M6-bc, floralginsenoside La, floralginsenoside Lb)
1078.59 (ginsensoside Rc, ginsensoside Rb2, ginsenoside Rb3, floralginsenoside M, floralginsenoside N)

Likewise, the residual water phase fractions enrich one or more oligosaccharides.

B. *Zingiber officinalis* Extract and Ethyl Acetate Fractions

*Zingiber officinalis* extract as obtained from Cactus Botanics Ltd. displayed greater % increase in RFU at a concentration of 100 μg/mL when compared to the $EC_{50}$ concentration of acetylcholine. Lower concentrations of *Zingiber officinalis* extract (i.e. 10 μg/mL) still result in about 75% of the % increase in RFU when compared to the $EC_{50}$ concentration of acetylcholine.

The ethyl acetate fraction of the *Zingiber officinalis* extract showed lesser % increase in RFU, but still exhibited over 200% increase in RFU in the first ethyl acetate fraction.

C. *Zingiber officinalis* and Residual Water Phase Fractions

The residual water phase fractions of *Zingiber officinalis* extract displayed at least 250% increase in RFU (which is over 75% of the increase by the $EC_{50}$ concentration of acetylcholine) and surprisingly showed greater or comparable % increase in RFU 100 μg/mL when compared to the $EC_{50}$ concentration of acetylcholine, especially for the first five fractions.

Even less concentrated fractions, e.g. 10 μg/mL, had comparable % increase in RFU (at least 75% of the increase) when compared to the $EC_{50}$ concentration of acetylcholine, especially for the first five fractions.

While not wishing to be bound by theory, the residual water phase fractions enrich one or more oligosaccharides which may include a tetrasaccharide comprising a dimer of disaccharides.

The examples and other embodiments described herein are exemplary and not intended to be limiting in describing the full scope of compositions and methods of this invention. Equivalent changes, modifications and variations of specific embodiments, materials, compositions and methods may be made within the scope of the present invention, with substantially similar results.

As used throughout, ranges are used as shorthand for describing each and every value that is within the range. Any value within the range can be selected as the terminus of the range. In addition, all references cited herein are hereby incorporated by referenced in their entireties. In the event of a conflict in a definition in the present disclosure and that of a cited reference, the present disclosure controls. Unless otherwise specified, all percentages and amounts expressed herein and elsewhere in the specification should be understood to refer to percentages by weight. The amounts given are based on the active weight of the material.

We claim:

1. An oral care composition that alleviates dry mouth comprising a dry mouth alleviating component,
   wherein the dry mouth alleviating component comprises an extract of Araliaceae which is an extract of *Panax ginseng* in an amount of from 0.15 to 0.75 wt % of the overall composition, and an orally acceptable vehicle,
   wherein the vehicle includes a water-phase with humectant
      wherein the humectant comprises propylene glycol and wherein the propylene glycol is present in the amount of from 10 to 30 wt % of the overall composition, and
   wherein the composition optionally further comprises other agent for increasing salivation, alleviating dry mouth or the sensations of dry mouth which is not an extract of Araliaceae, and a fluoride ion source.

2. The oral care composition of claim 1, wherein the extract of *Panax ginseng* is present in an amount selected from the group consisting of from 0.15% to 0.75% and 0.5%.

3. The oral care composition of claim 1, wherein the composition contains an amount of acetylcholine, pilocarpine, muscarine, arecoline, carbachol or bethanecol selected from the group consisting of not more that 0.01%; not more than 0.001%; not more than 0.0001%; and 0%.

* * * * *